United States Patent [19]

Yu et al.

[11] 4,021,538

[45] May 3, 1977

[54] METHOD FOR PRODUCING PIGMENTATION IN HAIR OR SKIN

[76] Inventors: Ruey J. Yu, 4400 Dexter St., Philadelphia, Pa. 19128; Eugene J. Van Scott, 1138 Sewell Lane, Rydal, Pa. 19046

[22] Filed: Sept. 29, 1975

[21] Appl. No.: 617,739

[52] U.S. Cl. .................. 424/60; 8/10.1; 424/63; 424/69
[51] Int. Cl.$^2$ .................. A61K 7/44; A61K 7/13
[58] Field of Search .............. 8/10.2; 424/60, 63, 424/309

[56] References Cited

UNITED STATES PATENTS

| | | | |
|---|---|---|---|
| 2,539,202 | 1/1951 | Peck | 8/10.2 |
| 2,875,769 | 3/1959 | Rosmarin et al. | 8/102 |

FOREIGN PATENTS OR APPLICATIONS 2,117,762  5/1972  Germany .................. 424/319

*Primary Examiner*—Dale R. Ore
*Attorney, Agent, or Firm*—LeBlanc & Shur

[57] ABSTRACT

A composition and method for producing pigmentation in skin or hair by topical application is described. The composition comprises as active ingredients one or more esters of DOPA wherein the esterifying radical is an alkyl, aryl or alkylene radical having up to 12 carbon atoms, or methyl dopate. The pigmentation producing ester is dissolved in a pharmaceutically acceptable vehicle which may be alkaline, neutral or acidic, and may contain peroxides or other oxidizing agents. Skin treated by topical application of the composition of this invention has been found to be protected against sun burn and against erythema from ultraviolet light in proportion to the extent of the pigmentation produced.

26 Claims, No Drawings

METHOD FOR PRODUCING PIGMENTATION IN HAIR OR SKIN

The hair and skin colors in animals and humans are primarily due to the pigments originally biosynthesized in the melanocytes of hair bulbs and skin epidermis. Pigments formed by mammalian melanocytes have been categorized as eumelanin (brown or black pigment) or phaeomelanin (yellow or red pigment) depending upon their color characteristics or solubility in dilute alkali. Both eumelanin and phaeomelanin are presumably synthesized via a common metabolic pathway in the earlier stages involving tyrosine, dopa and dopaquinone. A copper-dependent enzyme called tyrosinase has been found to catalyze the first two steps of the metabolic pathway.

It has been known for some time that a stimulation of pigment formation also known as melanogenesis may be triggered by hormones such as MSH (melanocyte stimulating hormones), drugs such as nitrogen mustard, and radiations such as X-ray and sunlight. The simplest and most reliable method of skin pigmentation, however, is by sunlight, known as suntan. Unfortunately, sunlight is also a major cause of skin cancer and other skin disorders, such as actinic keratosis. It is therefore imperative to search for harmless substances of physiologic origin capable of forming pigments in the skin for the purposes of both protection against sunlight and cosmetic appeal.

Commercially available products for skin pigmentation normally contain dihydroxyacetone as an active ingredient. This compound is known to bind to skin proteins to produce an unnatural yellowish color. There is virtually no commercial product available which can, by topical application, form or stimulate the formation of natural pigments in the skin.

In contrast, numerous products for altering hair color are available commercially. Hair dyes exist in varieties of color shades either giving temporary, semipermanent or so-called permanent hair color. These dyes consist primarily of azo dyes, anthraquinone dyes, aminophenols, and aromatic diamines and their nitro derivatives. However, most of these chemical compounds are potential allergens and have also been found, recently, to be mutagenic compounds on microorganisms. Furthermore, the long term use of azo dyes and certain aromatic amines carries a high risk of cancer. These compounds have been shown to be carcinogenic in animal tests.

3,4-Dihydroxyphenylalanine, DOPA, $C_9H_{11}NO_4$, M.W. 197, is a nontoxic and nonallergenic substance of physiologic origin. DOPA is biosynthesized from tyrosine in the melanocytes of hair and skin for pigmentation. DOPA itself is practically insoluble in water or lipid solvents, and therefore, when topically applied it will penetrate the skin or hair only slightly. The esters of DOPA are, however, readily soluble in both water and lipid solvents. It has now been discovered, as will be subsequently described, that certain DOPA esters are highly effective agents for skin and hair pigmentation.

Accordingly, it is an object of this invention to provide a cosmetic composition for producing pigmentation utilizing a nontoxic, nonallergenic substance of physiologic origin.

It is another object to provide a cosmetic composition for producing pigmentation in hair and skin containing an ester of the nontoxic, nonallergenic substance DOPA which will rapidly penetrate the skin and/or hair to produce desired pigmentation.

It is still another object to provide a method for producing pigmentation in hair or skin by topical application of an ester of DOPA in a pharmaceutically acceptable vehicle.

It is still another object of this invention to provide a method for producing pigmentation in hair or skin by topical application of an ester of DOPA in a pharmaceutically acceptable vehicle, followed by subsequent applications of an alkaline, buffered alkaline, or solution containing an oxidizing agent.

In accordance with the present invention, the following chemical compounds are incorporated in compositions for topical application, in dextro, levo, or mixed dextro and levo forms, to produce skin and hair pigmentation:

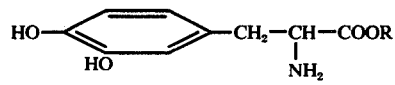

wherein R is an alkyl, aryl or alkylene radical having up to 12 carbon atoms.

These compounds may be incorporated in cosmetic compositions as either free bases or forms of HCl, $H_2SO_4$, $HNO_3$, or any other common acid, formed, for example, by dissolution of the free bases in acid solution.

Preferred compounds which have been found to be effective within the scope of the foregoing generic structure are listed below:

(1) DOPA methyl ester, wherein R = $CH_3$
(2) DOPA ethyl ester, wherein R = $C_2H_5$
(3) DOPA n-propyl ester, wherein R = $(CH_2)_2CH_3$
(4) DOPA isopropyl ester, wherein R = CH $(CH_3)_2$
(5) DOPA n-butyl ester, wherein R = $(CH_2)_3CH_3$
(6) DOPA iso-butyl ester, wherein R = $CH_2CH(CH_3)_2$
(7) DOPA sec-butyl ester, wherein R = $CH(CH_3)(C_2H_5)$
(8) DOPA n-amyl ester, wherein R = $(CH_2)_4 CH_3$
(9) DOPA iso-amyl ester, wherein R = $(CH_2)_2CH(CH_3)_2$
(10) DOPA glycerol ester, wherein R = $CH_2CHOH CH_2OH$
(11) DOPA propylene glycol ester, wherein R = $CH_2CHOH CH_3$
(12) DOPA benzyl ester, wherein R = $CH_2C_6H_5$
(13) DOPA lauryl ester, wherein R = $(CH_2)_{11} CH_3$
(14) DOPA cyclohexyl ester, wherein R = $C_6H_{11}$
(15) Methyl dopate (2- methyl DOPA ethyl ester)

The cosmetic compositions of this invention containing a preferred DOPA esters listed may be formulated according to one of the following methods:

I. In one method of the present invention, the compound is dissolved in alkaline aqueous or alkaline alcoholic solution. A golden yellowish to brownish color develops within a few minutes and intensifies with time. The colored solution may be applied directly to human or animal skin or hair or it may be acidified before such application. To enhance the penetration of the compound into the skin or hair, vehicles containing other ingredients such as alcohol acetone or propylene glycol may be used. The skin or hair so treated develops a tan color immediately and intensifies somewhat within a few hours. The rate of color development and its final intensity, which may vary from golden to dark brown, depend on the characteristics and concentration of the pigmenting agent.

II. In a second method of the present invention the DOPA ester pigmenting agent from the group defined above is dissolved in acidic, neutral or alkaline aqueous solution and a peroxide or other oxidizing agent is added to the solution. A golden yellowish to brownish color develops in the solution within a few hours and intensifies with time. The colored solution is then applied directly to the skin or hair. To enhance penetration of the compound into the skin or hair, vehicles containing other ingredients such as alcohols, acetone or propylene glycol may be used. The skin or hair so treated develops a tan color immediately. The rate of color development and the final intensity of the color produced is dependent on the concentration and characteristics of the pigmenting agent and the oxidizing agent.

III. In still another method within the scope of the present invention, a DOPA ester pigmenting agent from the foregoing group is dissolved in acidic or neutral aqueous or alcoholic aqueous solution, and the solution topically applied onto the skin or hair. The skin or hair develops a tan to orange brownish pigment after a subsequent application of (a) an alkaline or buffered alkaline solution alone or (b) a solution containing an oxidizing agent in acidic, neutral or alkaline aqueous or aqueous alcoholic solution.

Skin so colored with compositions of this invention will be protected against sunburn, and against erythema from ultraviolet light. The pigments formed by application of the compositions of the present invention show a wide absorption spectrum of between 260 and 500 nm in ultraviolet and visible lights.

The DOPA esters of this invention, useful for skin and hair pigmentation, may be synthesized by novel and relatively simple processes. DOPA esters, formed as their hydrochloride for convenience, are synthesized by the reaction of DOPA with alcohols in the presence of thionylchloride under the anhydrous conditions according to well known laboratory techniques.

The following is a detailed description of the skin and hair pigmenting process which comprise the present invention.

To produce skin or hair pigmentation, in accordance with the present invention and with compositions formulated according to method I above, any one of the preferred DOPA esters described above is dissolved in an alkaline aqueous, alkaline aqueous alcoholic, or alkaline alcoholic solution. The alkalis used may be inorganic or organic type. Inorganic alkalis used may be ammonium hydroxide, sodium bicarbonate, sodium carbonate, sodium hydroxide, sodium methoxide, sodium ethoxide, sodium borate, sodium phosphate and similar compounds of potassium. Organic alkalis used may be any base containing amine, ethanolamine or ethylenediamine groups such as monoethanolamine, diethanolamine, triethanolamine, N-methyldiethanolamine, ethylenediamine, isopropanolamine and tetraethanolammonium hydroxide.

Solutions thereof with water and/or alcohol such as ethanol may be prepared at room temperature. These solutions begin to turn golden yellow or brown in color within a few minutes. The color increases in intensity over the next few hours. The rate of color development and its final intensity is proportional to the concentration and characteristics of the DOPA ester in solution.

Generally, the concentration of DOPA ester may range from 0.1 to 10 weight % of the solution. The alkalinity of the solution may range from pH 8 to 10.

The solution then may be acidified with an acid such as hydrochloric acid to a human skin pH 5–6. The solution is then applied topically to the skin or hair. The skin or hair treated with this tanning solution develops a golden yellow to dark brown pigmentation immediately and intensifies within a few hours.

Referring specifically to the second of the above identified methods of formulation within the scope of the present invention, one of the DOPA esters described above is dissolved in a solution which may be acidic, neutral or alkaline aqueous; acidic, neutral or alkaline aqueous alcoholic; or acidic, neutral or alkaline alcoholic. Organic or inorganic peroxide, peracid or other oxidizing agent in an alcoholic or water solution is added. If the pigmentation agent is in acidic solution, the acid thereof may be hydrochloric acid, sulfuric acid, nitric acid, or another common acid. Alkalis used in alkaline pigmentation agent solutions may be inorganic or organic bases as described above. Organic or inorganic peroxide, peracid, or other oxidizing agent which may be used include benzoyl peroxide, perbenzoic acid, peracetic acid, hydrogen peroxide, ammonium persulfate, potassium persulfate, potassium chromate, potassium dichromate, potassium permanganate, periodic acid, sodium periodate, osmiun tetroxide, sodium hypochlorite and calcium hypochlorite.

Solutions prepared and stored at room temperature turn golden yellow or brown in color within a few days. The color increases in intensity over the next few days. The rate of color development and its final intensity is proportional to the concentration of the tanning material and the type of the oxidizing agent used as well as the pH of the solution.

Generally, the concentration of the DOPA ester may range from 0.1 to 10 weight % of the solution. The concentration of the oxidizing agent may range from 0.01 to 1 weight % of the solution. The concentration of ethanol may range from 0 to 95 volume % of the solution and the pH may range from 3 to 11. The solution may of course be neutralized or acidified to pH 5–6 prior to application. After topical application with this tanning solution the skin or hair develops a golden yellow to brown pigmentation immediately and may intensify within a few hours.

With reference to the third of the above identified methods within the scope of the present invention, one of the DOPA esters is dissolved in acidic or neutral aqueous, acidic or neutral aqueous alcoholic, or acidic or neutral alcoholic solutions, without an oxidizer included therein. A few minutes after topical application, as the solvent penetrates or evaporates, the skin or hair is treated with an alkaline or preferably buffered alkaline solution alone, or an oxidizing agent in aqueous, aqueous alcoholic or alcoholic solution. The pH of this solution may range from 3 to 11. The concentrations of the oxidizing agent and the other solution components are the same as in the foregoing methods. The aforementioned buffered alkaline solution includes organic and/or inorganic buffered alkalis, more specifically an amino acid and an alkali such as tyrosine-KOH, glycine-NaOH, and aspartic acid - NaOH. The skin or hair treated in this manner develops a golden yellow to brownish pigment slowly over several hours.

The effectiveness of the tanning agents of this invention for topical usage on the skin and hair may be enhanced when vehicles with ingredients such as ethyl alcohol, propylene glycol or acetone are included in the tanning solution. While the concentration of ethyl alcohol may approach 95% of the tanning solution, the concentration of propylene glycol should not exceed 30% of the solution by volume.

Vehicles other than solutions may also be successfully used in the present invention for hair and skin tanning. The tanning ingredients may be incorporated in lotions, creams, ointments or may be in powder form. The conditions used for the tanning of skin and hair are the same as described above in conjunction with solutions of the DOPA esters of this invention.

Generally, the skin and hair color can be made to approximate various shades of natural pigmentation from golden yellow to dark brown and brown-black. The skin so colored with the aforementioned processes is protected against sunburn and against erythema from ultraviolet light. As already mentioned earlier, the pigments formed by the processes of the present invention show a wide absorption spectrum between 260 and 500 nm in ultraviolet and visible lights. For example, the pigments produced from DOPA methyl ester 1% and ammonium hydroxide 1% in aqueous alcoholic solution after 5 minutes at room temperature had the following molar extinction coefficients: 3,270 at 280 nm, 2,640 at 300 nm and 1,900 at 320 nm.

In a variation of the foregoing methods two or more than two DOPA esters may be utilized to produce desired color shades of pigments in the skin or hair.

The following are illustrative examples of formulations of compositions and pigmentation processes according to this invention. Although the examples utilize only selected members of the above list of preferred compounds useful according to this invention, it should be understood that the following examples are illustrative and not limited. Therefore, any of the above compounds may be substituted according to the teachings of this invention in the following formulations and processes.

EXAMPLE 1

Pigmentation with DOPA methyl ester

D, L-DOPA methyl ester hydrochloride was dissolved in water, and ethyl alcohol was then added to make 50% by volume in alcohol content. The solution was alkalinized to pH8 with 2N NaOH. With concentrations of DOPA methyl ester in various solutions from 0.2 to 1.0% by weight, the solution turned brownish within a few minutes and showed a wide absorption spectrum between 260 and 500 nm in ultraviolet and visible lights. After five minutes these solutions had the following molar extinction coefficients: 3,270 at 280 nm, 2,640 at 300 nm, and 1,900 at 320 nm. These solutions, acidified at pH 5 with 1 N HCl, were applied topically to human hair and skin and turned the hair and skin brownish immediately.

Areas of skin colored with this material and exposed to doses of ultraviolet light or sunlight that ordinarily would cause burning (redness and blistering) of lightly pigmented normal skin were protected against such effect. The degree of protection was proportional to the degree of skin tanning produced. Skin colored by these materials was protected to a degree equivalent to that of skin of the same color due to natural pigment.

EXAMPLE 2

Skin pigments produced from DOPA esters and benzoyl peroxide

L-DOPA ester hydrochlorides and methyl dopate hydrochloride (each in different experiments) was dissolved in ethyl alcohol. To this solution was added benzoyl peroxide and water. The final concentration of DOPA material, benzoyl peroxides and ethyl alcohol were 0.2%, 0.1% and 80% respectively. The pH of the solution was 5. Within a few hours, the solution turned light brownish and this color increased in intensity to brownish over the next few days. When this solution was applied topically to human hair and skin, it turned the hair and skin brownish immediately.

EXAMPLE 3

Skin and hair pigments produced from methyl dopate and DOPA esters with persulfate Each of the pigmenting agents to be tested in this series of experiments was dissolved in water, and a solution of ammonium or potassium persulfate in water was added. Ethyl alcohol was then added to make the final concentration of the pigmentation agent, the persulfate and the alcohol 0.2%, 0.1%, and 50% respectively. The solution turned brown or orange reddish within a few hours. When applied topically to human skin and hair, it turned the skin and hair brownish or red brownish immediately.

EXAMPLE 4

Skin and hair pigments produced from methyl dopate and DOPA esters with periodic acid or periodate Each of the pigmentation agents to be tested in this series of experiments was dissolved in water. Ethyl alcohol was then added to make a 50% alcoholic solution with a pigmentation agent concentration of 1% and a solution of pH5. This solution was applied topically to human skin. As the solvent evaporated, aqueous or aqueous alcoholic solution of 1% periodic acid or solium periodate was applied on the same area of skin. The skin thus treated developed brownish or reddish pigments immediately.

EXAMPLE 5

Skin and hair pigments produced from methyl dopate and DOPA esters with dichromate Using the procedure of Example 4, an aqueous solution of 1% potassium or sodium dichromate was used instead of the periodic acid. The skin thus treated developed yellow brownish pigment immediately. The color increased in intensity to dark brownish over the next few minutes.

EXAMPLE 6

Pigmentation method involving subsequent treatment with alkaline material

One of the preferred DOPA esters or methyl dopate was dissolved in a mixture of water, ethanol and propylene glycol (40, 50, 10) to make 2% in solution. The solution was applied to the skin or hair. A few minutes after topical application, as the solvent penetrated or evaporated, the skin or hair was treated with a buffered alkaline solution such as 0.1 M tyrosine-KOH, 0.1 M tyrosine - NaOH pH 11 or 2% aspartic acid - 4% ethanolamine pH 10. Gradual tanning of the skin or hair occurred during the ensuing few hours. It was also found that the degree of tanning could be enhanced by repeated application of the solution as described immediately above.

EXAMPLE 7

Pigmentation method involving subsequent treatment with ammonium persulfate

One of the preferred DOPA esters or methyl dopate was dissolved in a mixture of water, ethanol and propylene glycol (40, 50, 10) to make 2% in solution. The solution was applied to the skin or hair. A few minutes after topical application, as the solvent penetrated or evaporated, the skin or hair was topically treated with 0.4% ammonium persulfate in a mixture of water, ethanol and propylene glycol (40, 50 10). Gradual tanning of the skin or hair to a reddish brown occurred during the following few hours.

EXAMPLE 8

Pigmentation method involving subsequent treatment with periodic acid

One of the preferred DOPA esters or methyl dopate was dissolved in a mixture of water, ethanol and propylene glycol (40, 50, 10) to make 1% in solution. The solution was applied to the skin or hair. A few minutes after topical application, as the solvent penetrated or evaporated, the skin or hair was topically treated with 0.1% periodic acid in a mixture of water and ethanol (50, 50). Immediate pigmentation to reddish brown of the skin or hair occured within a few minutes. The skin or hair so treated developed a reddish brownish pigment during the ensuing few hours.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by United States Letters Patent is:

1. A method for producing pigmentation in hair or skin comprising: topically applying to preselected areas of the body, a composition comprising an effective pigmentation producing amount of at least one DOPA ester selected from the group consisting of esters having the formula

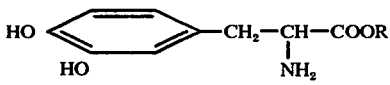

wherein R is an alkyl, aryl or alkylene radical having from 1 to 12 carbon atoms, and methyl dopate in a pharmaceutically acceptable vehicle.

2. The method of claim 1 wherein R is a member selected from the group consisting of methyl, ethyl, n-propyl, isopropyl, n-butyl, iso-butyl, sec-butyl, n-amyl, iso-amyl, glycerol, propylene glycol, benzyl, lauryl, and cyclohexyl.

3. The method of claim 2 wherein said ester is present in said composition in from 0.1 to 10 percent by weight.

4. The method of claim 3 wherein said vehicle comprises an alkaline solvent selected from the group consisting of ammonium hydroxide, sodium bicarbonate, sodium carbonate, sodium hydroxide, sodium methoxide, sodium ethoxide, sodium borate, sodium phosphate, potassium bicarbonate, potassium carbonate, potassium hydroxide, potassium methoxide, potassium ethoxide, potassium borate, potassium phosphate, monoethanolamine, diethanolamine, triethanolamine, N-methyldiethanolamine, ethylenediamine, isopropanolamine and tetraethanolammonium hydroxide.

5. The method of claim 4 wherein the vehicle further comprises ethyl alcohol present in up to 95 percent by volume of the solvent.

6. The method of claim 4 wherein the vehicle further comprises water present in up to 95 percent by volume of the solvent.

7. The method of claim 4 wherein the solvent has an initial pH of from 8 to 10.

8. The method claim 4 further comprising neutralizing said composition to a pH of from 5–6 before topical application thereof.

9. The method of claim 3 wherein said vehicle comprises an aqueous solution of an acid selected from the group consisting of HCl, $H_2SO_4$, and $HNO_3$ at a pH of from 3–6.

10. The method of claim 3 wherein said vehicle comprises a solution of an acid selected from the group consisting of HCl, $H_2SO_4$ and $HNO_3$ in ethyl alcohol, said alcohol present in up to 95% of said composition, by volume.

11. The method of claim 1 wherein said vehicle is water.

12. The method of claim 1 in which said vehicle further comprises an oxidizing agent selected from the group consisting of benzoyl peroxide, perbenzoic acid, peracetic acid, hydrogen peroxide, ammonium persulfate, potassium persulfate, potassium chromate, potassium dichromate, potassium permanganate, periodic acid, sodium periodate, osmium tetroxide, sodium hypochlorite and calcium hypochlorite, present in from 0.1 to 1% by weight of said composition.

13. The method of claim 5 wherein said vehicle further comprises an oxidizing agent selected from the group consisting of benzoyl peroxide, perbenzoic acid, peracetic acid, hydrogen peroxide, ammonium persulfate, potassium persulfate, potassium chromate, potassium dichromate, potassium permanganate, periodic acid, sodium periodate, osmium tetroxide, sodium hypochlorite and calcium hypochlorite, present in from 0.1 to 1% by weight of said composition.

14. The method of claim 6 wherein said vehicle further comprises an oxidizing agent selected from the group consisting of benzoyl peroxide, perbenzoic acid, peracetic acid, hydrogen peroxide, ammonium persulfate, potassium persulfate, potassium chromate, potassium dichromate, potassium permanganate, periodic acid, sodium periodate, osmium tetroxide, sodium hypochlorite and calcium hypochlorite, present in from 0.1 to 1% by weight of said composition.

15. The method of claim 9 wherein said vehicle further comprises an oxidizing agent selected from the group consisting of benzoyl peroxide, perbenzoic acid, peracetic acid, hydrogen peroxide, ammonium persulfate, potassium persulfate, potassium chromate, potassium dichromate, potassium permanganate, periodic acid, sodium periodate, osmium tetroxide, sodium hypochlorite and calcium hypochlorite, present in from 0.1 to 1% by weight of said composition.

16. The method of claim 10 wherein said vehicle further comprises an oxidizing agent selected from the group consisting of benzoyl peroxide, perbenzoic acid, peracetic acid, hydrogen peroxide, ammonium persulfate, potassium persulfate, potassium chromate, potassium dichromate, potassium permanganate, periodic acid, sodium periodate, osmium tetroxide, sodium hypochlorite and calcium hypochlorite, present in from 0.1 to 1% by weight of said composition.

17. The method of claim 11 wherein said vehicle further comprises an oxidizing agent selected from the group consisting of benzoyl peroxide, perbenzoic acid, peracetic acid, hydrogen peroxide, ammonium persulfate, potassium persulfate, potassium chromate, potassium dichromate, potassium permanganate, periodic acid, sodium periodate, osmium tetroxide, sodium hypochlorite and calcium hypochlorite, present in from 0.1 to 1% by weight of said composition.

18. The method of claim 9 further comprising subsequently topically applying a buffered alkaline solution selected from the group consisting of tyrosine-KOH, glycine-NaOH, and aspartic acid-NaOH having a pH of from 3 to 11.

19. The method of claim 10 further comprising subsequently topically applying a buffered alkaline solution selected from the group consisting of tyrosine-KOH, glycine-NaOH, and aspartic acid-NaOH having a pH of from 3 to 11.

20. The method of claim 11 further comprising subsequently topically applying a buffered alkaline solution selected from the group consisting of tyrosine-KOH, glycine-NaOH, and aspartic acid-NaOH having a pH of from 3 to 11.

21. The method of claim 9 further comprising subsequently topically applying an alkaline solution selected from the group consisting of ammonium hydroxide, sodium bicarbonate, sodium carbonate, sodium hydroxide, sodium methoxide, sodium ethoxide, sodium borate, sodium phosphate, potassium bicarbonate, potassium carbonate, potassium hydroxide, potassium methoxide, potassium ethoxide, potassium borate, potassium phosphate, monoethanolamine, diethanolamine, triethanolamine, N-methyldiethanolamine, ethylenediamine, isopropanolamine and tetraethanolammonium hydroxide said solution having a pH of from 6 to 11.

22. The method of claim 10 further comprising subsequently topically applying an alkaline solution selected from the group consisting of ammonium hydroxide, sodium bicarbonate, sodium carbonate, sodium hydroxide, sodium methoxide, sodium ethoxide, sodium borate, sodium phosphate, potassium bicarbonate, potassium carbonate, potassium hydroxide, potassium methoxide, potassium ethoxide, potassium borate, potassium phosphate, monoethanolamine, diethanolamine, triethanolamine, N-methyldiethanolamine, ethylenediamine, isopropanolamine and tetraethanolammonium hydroxide said solution having a pH of from 6 to 11.

23. The method of claim 11 further comprising subsequently topically applying an alkaline solution selected from the group consisting of ammonium hydroxide, sodium bicarbonate, sodium carbonate, sodium hydroxide, sodium methoxide, sodium ethoxide, sodium borate, sodium phosphate, potassium bicarbonate, potassium carbonate, potassium hydroxide, potassium methoxide, potassium ethoxide, potassium borate, potassium phosphate, monoethanolamine, diethanolamine, triethanolamine, N-methyldiethanolamine, ethylenediamine, isopropanolamine and tetraethanolammonium hydroxide said solution having a pH of from 6 to 11.

24. The method of claim 9 further comprising subsequently applying topically a solution containing an oxidizing agent selected from the group consisting of benzoyl peroxide, perbenzoic acid, peracetic acid, hydrogen peroxide, ammonium persulfate, potassium persulfate, potassium chromate, potassium dichromate, potassium permanganate, periodic acid, sodium periodate, osmium tetroxide, sodium hypochlorite and calcium hypochlorite present in from 0.1 to 1% by weight of said solution.

25. The method of claim 10 further comprising subsequently applying topically a solution containing an oxidizing agent selected from the group consisting of benzoyl peroxide, perbenzoic acid, peracetic acid, hydrogen peroxide, ammonium persulfate, potassium persulfate, potassium chromate, potassium dichromate, potassium permanganate, periodic acid, sodium periodate, osmium tetroxide, sodium hypochlorite and calcium hypochlorite present in from 0.1 to 1% by weight of said solution.

26. The method of claim 11 further comprising subsequently applying topically a solution containing an oxidizing agent selected from the group consisting of benzoyl peroxide, perbenzoic acid, peracetic acid, hydrogen peroxide, ammonium persulfate, potassium persulfate, potassium chromate, potassium dichromate, potassium permanganate, periodic acid, sodium periodate, osmium tetroxide, sodium hypochlorite and calcium hypochlorite present in from 0.1 to 1% by weight of said solution.

* * * * *